United States Patent
Kashyap et al.

(10) Patent No.: US 9,072,732 B2
(45) Date of Patent: Jul. 7, 2015

(54) INDICATION FOR USE OF NIACIN (NICOTINIC ACID) FOR TREATMENT AND REVERSAL OF FATTY LIVER DISEASE

(75) Inventors: Moti L. Kashyap, Rancho Palos Verdes, CA (US); Vaijinath S. Kamanna, Irvine, CA (US); Shobha V. Kamanna, Irvine, CA (US)

(73) Assignees: The Regents of the University of California, Oakland, CA (US); Veterans Affairs Health Care System, Long Beach, CA (US)

( * ) Notice: Subject to any disclaimer, the term of this patent is extended or adjusted under 35 U.S.C. 154(b) by 0 days.

(21) Appl. No.: 13/988,972

(22) PCT Filed: Nov. 22, 2011

(86) PCT No.: PCT/US2011/061931
§ 371 (c)(1),
(2), (4) Date: Jul. 23, 2013

(87) PCT Pub. No.: WO2012/071459
PCT Pub. Date: May 31, 2012

(65) Prior Publication Data
US 2013/0303548 A1 Nov. 14, 2013

Related U.S. Application Data

(60) Provisional application No. 61/416,176, filed on Nov. 22, 2010.

(51) Int. Cl.
*A61K 31/44* (2006.01)
*A61K 31/455* (2006.01)
*A61K 45/06* (2006.01)
*C07D 213/80* (2006.01)

(52) U.S. Cl.
CPC .............. *A61K 31/455* (2013.01); *A61K 45/06* (2013.01); *C07D 213/80* (2013.01)

(58) Field of Classification Search
CPC .................................................. A61K 31/455
USPC ........................................................ 514/356
See application file for complete search history.

(56) References Cited

U.S. PATENT DOCUMENTS

2007/0105793 A1 5/2007 Hendrix
2007/0161578 A1 7/2007 Hwa et al.

OTHER PUBLICATIONS

Contermans et al., "Combination drug therapy in the treatment of severe hyperlipidaemia", Atherosclerosis, vol. 97, Supplement., S21-S26 (1992).*
Doege H, et al. Silencing of hepatic fatty acid transporter protein 5 in vivo reverses diet-induced non-alcoholic fatty liver disease and improves hyperglycemia, J. Biol. Chem. 283:22186-22192, 2008.
Samuel VT, et al. Mechanism of hepatc insulin resistance in non-aloholic fatty liver disease, J. Biol. Chem. 279:32345-32353, 2004.
Postic C, Girard J. Contribution of de novo fatty acid synthesis to hepatic steatosis and insulin resistance: lessons from genetically engineered mice. J. Clin. Invest. 118:829-838, 2008.
Adams LA, Lindor KD. Nonalcoholic fatty liver disease. Ann. Epidemiol. 7:863-869, 2007.
Yamaguchi K. et al. Inhibiting triglyceride synthesis improves hepatic steatosis but exacerbates liver damage and fibrosis in obese mice with non-alcoholic steatohepatitis. Hepatology 45:1366-1374, 2007.
Abdelmalek MF, Diehl AM. Nonalocoholic fatty liver disease as a complication of insulin resistance. Med. Clin. North Am. 91:1125-1149, 2007.
Charlton M. Nonalcoholic fatty liver disease: a review of current understanding and future impact. Clin. Gatroenterol. Hepatol. 2:1048-1058, 2004.
Pagano G, Pacinin M, Musso G, et al. Nonalcoholic steatohepatitis, insulin resistance, and metabolic syndrome: further evidence for an etiologic association. Hepatology 35:367-372, 2002.
Day CP, James OF. Hepatic steatosis: Innocent bystander or guilty party? Hepatology 27:1463-1466, 1998.
Day CP, James OF. Steatohepatitis: a tale of two "hit"? Gastroenterology. 114:842-845, 1998.
Wanless IR, Lentz JS. Fatty liver hepatitis (steatohepatitis) and obesity: an autopsy study with analysis of risk factors. Hepatology 12:1106-1110, 1990.
Ludwig J, Viggiano TR, McGill DB, Ott BJ. Nonalcoholic steatohepatitis: Mayo clinic experience with a hitherto unnamed disease. Mayo Clinic Proc. 55:434-438, 1980.
Adams LA, Angulo P. Treatment of non-alcoholic fatty liver disease. Postgrad. Med. J., 82:315-322, 2006.
Ahmed MH, Byrne CD. Current treatment of non-alcoholic fatty liver disease. Diabetes, Obesity and Metabolism. 11:188-195, 2009.
Belfort R, Harrison SA, Brown AK, el al. A placebo-controlled trial of pioglitazone in subjects with non-alcoholic steatohepatitis. N. Eng. J. Med. 355:2297-2307, 2006.
Sanyal A, Chalasani N, Kowdey KV, Pioglitazone, vitamin E, or placebo for nonalcoholc steatohepatitis. N. Eng. J. Med. 362:1675-1685, 2010.
Caldwell SH, Hespenheide EE, Dedick JA, Iezzoni JC, Battle EH, Shppard BL. A pilot study of thiazolidinedione, troglitazone, in non-alcoholic steatoheatatitis. Am. J. Gastroenterol. 96:519-525, 2001.
Neuschwander-Tetri BA, Brunt EM, Wehmeier KR, Oliver D, Bacon BR. Improved nonalcoholic steatohepatitis after 48 weeks of treatment with the PPAr-gamma ligand rosiglitazone. Hepatology 38:1008-1017, 2003.
Sanyal AJ, Mofrad PS, Contos MJ, et al. A pilot study of vitamin E versus vitamin E and pioglitazone for the treatment of nonalcoholic steatohepatitis. Clin. Gastroenerol. Hepatol, 2:1107-1115, 2004.
Lavine JE. Vitamin E treatment of nonalcoholic steatohepatitis in children: a pilot study, J. Pediatr. 136:734-738, 2000.
Harrison SA, Torgerson S, Hayashi P, Ward J, Schenker S. Vitamin E and vitamin C treatment improves fibrosis in patients with nonalcoholic steatohepatitis. Am. J. Gastroenterol. 98:2485-2490, 2003.
Carmiel-Haggai M, Cederbaum Al, Nieto N. A high-fat diet leads to the progression of non-alcoholic fatty liver disease in obese rats. FASEB J. 19:136-138, 2005.

(Continued)

*Primary Examiner* — Kevin E Weddington
(74) *Attorney, Agent, or Firm* — Berliner & Associates

(57) ABSTRACT

Niacin prevents and/or reverses the development of experimental hepatic steatosis, deposition of triglycerides in liver and serum of individuals, deposition of total cholesterol in liver and serum in individuals, and inhibit liver lipid peroxidation and oxidative stress in individuals at risk of developing fatty liver disease or NAFLD. In cultured human hepatocytes, niacin inhibits alcohol-induced fat accumulation.

12 Claims, 9 Drawing Sheets

(56) References Cited

OTHER PUBLICATIONS

Lieber CS, Leo MA, Mak KM, Xu Y, Cao Q, Ren C, Ponomarenko A, DeCarli LM. Model of nonalcoholic steatohepatitis. Am. J. Clin. Nutr. 79:502-509, 2004.

Charbonneau A, Unson CG, Lavoie J-M. High-fat diet-induced hepatic steatosis reduces glucagon receptor content in rat hepatocytes: potential interaction with acute exercise, J. Physiol. 579:255-267, 2007.

Choi CS, Savage DB, Kulkarni A, et al. Suppression of diacylglycerol acyltransferase-2 (DGAT2), but not DGAT1, with antisense oligonucleotides reverse diet-induced hepatic steatosis and insulin resistance. J. Biol. Chem. 282:22678-22688, 2007.

Hong XZ, Li LD, Wu LM. Effects of fenofibrate and xuezhikang on high-fat diet-induced non-alcoholic fatty liver disease. Clin. Expt. Pharmacol. Physiol. 34:27-35, 2007.

Hernandez M, Wright SD, Cai TQ. Critical role of cholesterol ester transfer protein in nicotinic acid-mediated HDL elevation in mice, Biochem. Biophys. Res. Commun. 355:1075-1080, 2007.

Fabbrini E, Mohammed BS, Korenblat KM, Magkos F, Magkos F, McCrea J, Patterson BW, Klein S. Effect of fenofibrate and niacin on intrhepatic triglyceride content, very-low density lipoprotein kinetics, and insulin action in obese subjects with nonalcoholic fatty liver disease. J. Clin. Endocrinol. Metab. 95:2727-2735, 2010.

PCT Search Report issued Mar. 29, 2012 in connection with related PCT Application No. PCT/US2011/061931.

* cited by examiner

A

B

A

B

A

B

US 9,072,732 B2

INDICATION FOR USE OF NIACIN (NICOTINIC ACID) FOR TREATMENT AND REVERSAL OF FATTY LIVER DISEASE

CROSS REFERENCE TO RELATED APPLICATIONS

The present application is claims priority to U.S. provisional application No. 61/416,176, filed on Nov. 22, 2010, which is hereby incorporated by reference in its entirety.

FIELD OF THE INVENTION

The invention relates generally to the prevention or treatment of fatty liver disease. More particularly, it relates to the use of niacin (nicotinic acid) to treat and reverse fatty liver disease.

BACKGROUND OF THE INVENTION

Fatty liver has become a major cause of liver disease, and causes of fatty liver disease include excess consumption alcohol, non-alcohol mediated metabolic abnormalities, and viral infections. For example in the US, more than 10% of people abuse or are dependent on alcohol, and more than 90% of people consuming excess alcohol develop alcoholic fatty liver disease (AFLD). Non-alcoholic fatty liver disease (NAFLD) is a serious health problem and gaining increasing recognition as a pathobiological component of obesity, type 2 diabetes, and metabolic syndrome. The worldwide prevalence of NAFLD is presently estimated at 30% of the general population, and it affects majority (up to 75%) of patients with obesity and type 2 diabetes (1, 2). NAFLD generally refers to a spectrum of liver damage ranging from simple fatty liver (hepatic steatosis), with benign prognosis, to a potentially progressive form, non-alcoholic steato-hepatitis (NASH), which may lead to liver fibrosis and cirrhosis (3). If untreated, NAFLD may lead to liver dysfunction, cirrhosis and its complications (eg. gastro-intestinal hemorrhage, ascites, etc), end-stage liver disease, need for liver transplantation. It is often associated with increased risk for developing cardiovascular disease resulting in increased morbidity and mortality. The clinical diagnosis of NAFLD is usually made based on clinical history and laboratory findings including, high transaminase levels, elevated body mass index (BMI), ultrasound evidence of fat, and features of metabolic syndrome. However, a liver biopsy is required to determine the severity of the disease and presence of NASH, and to assess the degree of fibrosis (4).

Despite its severity and prevalence in patients with obesity, type 2 diabetes, and metabolic syndrome, little is known about the pathogenesis of NAFLD and treatment modalities. Excessive accumulation of triglycerides in hepatocytes is the hallmark of NAFLD, which is strongly associated with hepatic insulin resistance (5-7). Increased triglyceride synthesis has been shown in fatty livers that accompany obesity and type 2 diabetes in humans and mice (8). Using animal models, it was shown that hepatic fat accumulation leads to hepatic insulin resistance by stimulating gluconeogenesis and activating PKC-ε and JNK1 signaling pathways (2). In regards to understanding the pathogenesis of NAFLD, several studies focused on whether hepatic steatosis plays any direct causal role in progression to advanced disease NASH or simply an innocent bystander in the pathogenesis of NAFLD. A two-hit hypothesis has been proposed to understand the pathogenesis of NAFLD: first hit includes excess fat accumulation in the liver, and second hit consist of oxidative stress and lipid peroxidation with increased generation of inflammatory cytokines (8-10). Several studies indicate that hepatic steatosis is a risk factor for NASH and fibrosis, and implicate steatosis as a direct contributor to the progressive NASH and fibrosis (reviewed in 9-12).

Currently, there are no established and recommended pharmacologic agents available for the treatment for NAFLD. Modifications of risk factors, such as weight reduction and dietary fat consumption are commonly recognized treatment modalities for NAFLD (reviewed in 13, 14). Numerous pilot studies have indicated that insulin sensitizers such as thiazolidinediones and antioxidants such as vitamin E improve clinical and histological features of NASH (15-21). Because of the lack of larger clinical trials, the value of these drugs for the treatment of NASH remains uncertain.

BRIEF SUMMARY OF THE INVENTION

Currently, there is no specific therapeutic agent for prevention or treatment of the various forms of fatty liver disease. A clinical trial to determine whether niacin can prevent or regress fatty liver disease has never been carried out except for one trial with niacin for only 16 weeks in patients with established non-alcoholic fatty liver disease. In this small clinical trial in 9 patients with existing NAFLD, administration of niacin (2000 mg/d) for only 16 weeks did not decrease intrahepatic triglyceride content, an index of hepatic steatosis and NAFLD. In contrast to this study, our observation in rat model of NAFLD indicated that niacin prevents the development of hepatic steatosis and NAFLD.

In one embodiment, a method for preventing the development of and/or treating and/or reversing fatty liver disease and/or NAFLD or associated with the complication of hepatitis (NASH) is provided comprising providing a composition comprising an effective amount of niacin, or its metabolites, or derivatives thereof, to an individual recognized to be in need of treatment.

In one embodiment, "subjects in need of treatment" as used herein includes subjects who have or show signs/symptoms that include, but are not limited to, clinical obesity, type 2 diabetes, clinical hepatomegaly, high transaminase levels, abnormal liver function tests, elevated body mass index, insulin resistance; on a high-fat diet; elevated fat accumulation in the liver; hepatomegaly; metabolic syndrome; fat and liver inflammation; and liver fibrosis, or any combination thereof. Such symptoms can be determined or observed upon using one or more clinical, laboratory or research tests/assays including but not limited to, family history indications; physical examination; imaging testing (including ultrasound and magnetic resonance imaging (MRI)); organ function tests; biopsys; and other tests as considered appropriate by the physician or provider for the subject. These same tests would be used to determine whether there was a reduction, inhibition or a prevention in these symptoms.

In another embodiment, "such subjects in need of treatment" also include those subjects already suffering from FLD, NAFLD, or AFLD. In one embodiment, niacin would be given to these subjects to reduce or reverse the nature of their symptoms, or degree of their various symptoms, which include but are not limited to deposition of triglycerides in liver and serum; and hepatic steatosis.

In another embodiment, such "subjects in need of treatment" also include those subjects at risk of developing fatty liver and/or NAFLD, complicated by hepatitis including non-alcoholic steato hepatitis (NASH).

The clinical diagnosis of NAFLD is usually made based on clinical history and laboratory findings including, high transaminase levels, elevated body mass index (BMI), ultrasound evidence of fat, and features of metabolic syndrome. However, a liver biopsy may be required to determine the severity of the disease and presence of NASH, and to assess the degree of fibrosis (4).

In one embodiment, subjects in need of treatment for fatty liver disease (FLD) will be identified using the clinical signs/symptoms and laboratory tests as indicated above in the four immediately preceeding paragraphs and once the diagnosis is made, they would be treated with niacin, or its metabolites, or derivatives or formulations thereof prophylactically or therapeutically for prevention of FLD or NAFLD, reduction in the FLD or NAFLD symptoms, or reversal of FLD or NAFLD.

In yet another embodiment, the effective amount of niacin, or its metabolites, or derivatives thereof, is given via enteral or parenteral routes of administration.

In yet another embodiment, a method for preventing and/or treating hepatic steatosis in individuals at risk of developing FLD or NAFLD is provided, comprising providing a composition comprising niacin, or its metabolites, or derivatives thereof, to an individual recognized to be in need of treatment.

In another embodiment, a method for preventing, treating and/or reversing deposition of triglycerides in liver and serum of individuals at risk of developing fatty liver or NAFLD is provided, comprising providing a composition comprising niacin, or its metabolites, or derivatives thereof, to an individual recognized to be in need of treatment.

In another embodiment, a method for preventing, treating and/or reversing deposition of triglycerides in liver cells is provided comprising providing a composition comprising niacin, or its metabolites, or derivatives thereof, to an individual recognized to be in need of treatment.

In yet a further embodiment, a method for preventing and/or reversing deposition of total cholesterol in liver and serum in individuals at risk of developing fatty liver and/or NAFLD is provided comprising providing a composition comprising niacin, or its metabolites, or derivatives thereof.

In yet a further embodiment, a method for preventing and/or reversing deposition of total cholesterol in liver cells is provided comprising providing a composition comprising niacin, or its metabolites, or derivatives thereof.

In a further embodiment, a method of preventing/inhibiting and/or reversing liver lipid peroxidation and inflammation in individuals at risk of developing fatty liver and/or NAFLD, complicated by hepatitis including non-alcoholic steato hepatitis (NASH) and other forms of steato hepatitis comprising providing a composition comprising niacin, or its metabolites, or derivatives thereof.

In another embodiment, a composition for preventing fatty liver and/or NAFLD disease in individuals at risk of developing fatty liver and/or NAFLD is provided, comprising an effective amount of niacin, or its metabolites, or derivatives thereof. In yet a further embodiment, the aforementioned composition is provided further comprising an acceptable pharmaceutical carrier or excipient known to those of skill in the art.

In one embodiment, a method for preventing the development of fatty liver disease in subjects in need of treatment is provided, comprising providing a composition comprising an effective amount of niacin, or its metabolites, or derivatives thereof.

In an embodiment of the method of the immediately preceeding paragraph, the fatty liver disease is alcoholic or non-alcoholic fatty liver disease.

In another embodiment of the method of the second preceding paragraph, those subjects show signs of obesity, type 2 diabetes, clinical hepatomegaly, high transaminase levels, abnormal liver function tests, elevated body mass index, insulin resistance; on a high-fat diet; elevated fat accumulation in the liver; hepatomegaly; metabolic syndrome; fat and liver inflammation; and liver fibrosis, or any combination thereof.

In yet another embodiment of the method of the third preceding paragraph, the effective amount of niacin is 0.5-3 g/daily in oral tablet form.

In one embodiment a method for preventing hepatic steatosis in subjects in need of treatment is provided, comprising providing a composition comprising niacin, or its metabolites, or derivatives thereof, to an individual recognized to be in need of treatment.

In another embodiment, a method for preventing deposition of triglycerides in liver and serum in subjects in need of treatment is provided, comprising providing a composition comprising niacin, or its metabolites, or derivatives In yet another embodiment, a method for preventing deposition of total cholesterol in liver and serum in subjects in need of treatment is provided comprising providing a composition comprising niacin, or its metabolites, or derivatives thereof.

In another embodiment, a method of inhibiting and/or reversing liver lipid peroxidation in subjects in need of treatment comprising providing a composition comprising niacin, or its metabolites, or derivatives thereof, to an individual recognized to be in need of treatment.

In yet another embodiment, a pharmaceutical, pharmaceutical composition or medicament for preventing fatty liver disease in subjects in need of treatment, comprising an effective amount of niacin, or its metabolites, or derivatives thereof.

In an embodiment of the pharmaceutical, pharmaceutical composition or medicament of the immediately preceding paragraph, the pharmaceutical, pharmaceutical composition or medicament further comprising an acceptable pharmaceutical carrier or excipient or a convention drug.

In an embodiment of the pharmaceutical, pharmaceutical composition or medicament of the second preceding paragraph, the fatty liver disease is alcoholic or non-alcoholic fatty liver disease.

In an embodiment of the pharmaceutical, pharmaceutical composition or medicament of the third preceding paragraph, the subjects show signs of obesity, type 2 diabetes, clinical hepatomegaly, high transaminase levels, abnormal liver function tests, elevated body mass index, insulin resistance; on a high-fat diet; elevated fat accumulation in the liver; hepatomegaly; metabolic syndrome; fat and liver inflammation; and liver fibrosis, or any combination thereof.

In another embodiment, a method of reducing or preventing macrosteatotic foci, is provided comprising niacin, or its metabolites, or derivatives thereof.

A method of reducing inhibiting liver thiobarbituric acid reactive substance levels] is provided comprising providing a composition comprising niacin, or its metabolites, or derivatives thereof.

BRIEF DESCRIPTION OF THE DRAWINGS

For a more complete understanding of the present invention, reference is now made to the following descriptions taken in conjunction with the accompanying drawing, in which:

As shown in FIG. 6, niacin (at 0.25 and 0.5 mM doses) significantly inhibited palmitic acid-induced fat accumulation by 32-35% in liver hepatocytes. P-values shown are compared to palmitic acid stimulated cells without pretreatment with niacin ($2^{nd}$ bar).

As shown in FIG. 7, treatment of HepG2 cells with niacin at 0.25 mM and 0.5 mM doses significantly inhibited palmitic acid-induced ROS production as assessed by measuring DCFDA fluorescence (a well established method for measuring $H_2O_2$, an index of oxidative stress). P-values shown are compared to palmitic acid stimulated cells without niacin ($2^{nd}$ bar).

Figure 6:
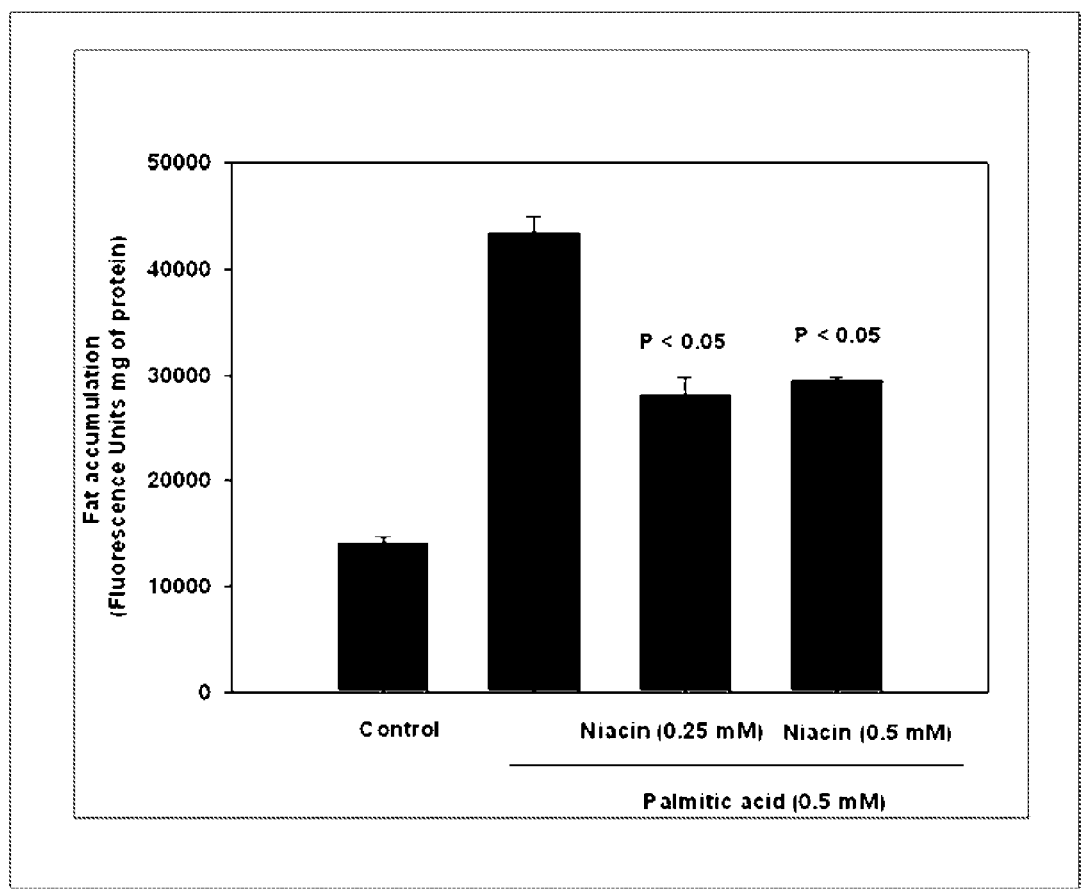
FIG. 6 shows niacin inhibits fat accumulation in human cultured hepatocytes (HepG2 cells). HepG2 cells were incubated with niacin (0-0.5 mM) for 24 h, and cells were then exposed to pathophysiologically relevant concentrations of palmitic acid (0.5 mM complexed with bovine serum albumin) for 24 h to stimulate the excessive fat accumulation in hepatocytes. Cells were then stained with Nile Red O for 5 min. Cellular lipid accumulation was assessed by measuring fluorescence.
Figure 7:
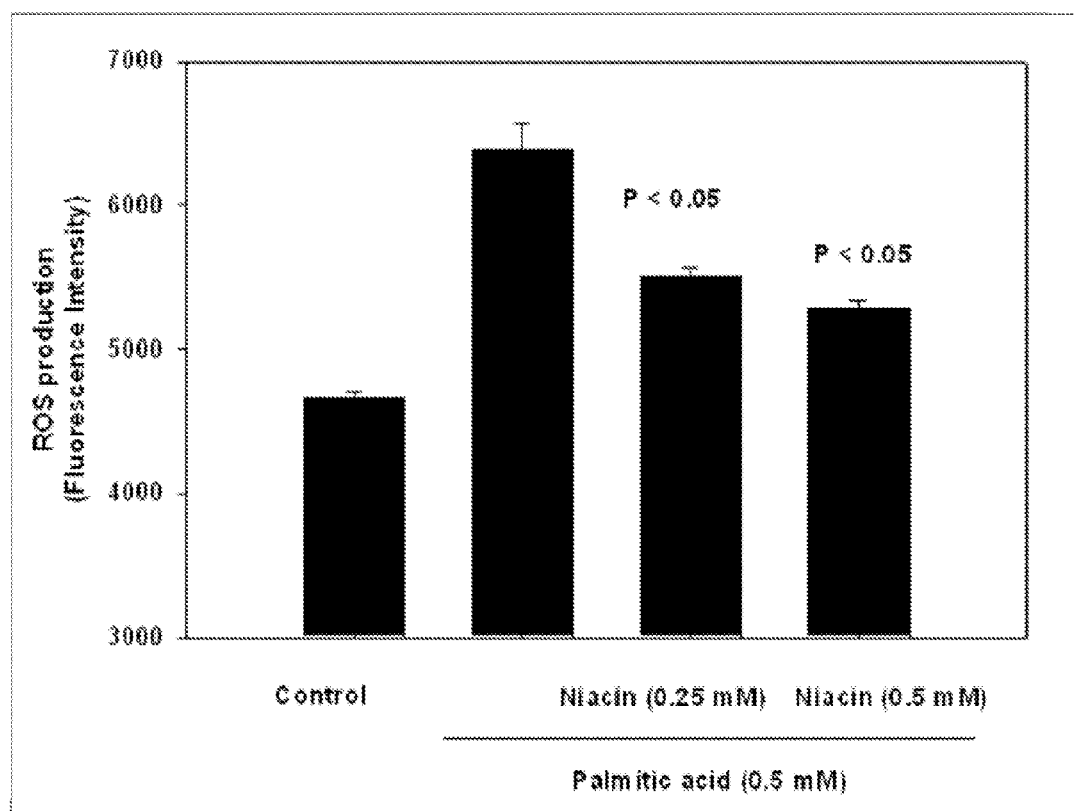
FIG. 7 shows niacin inhibits oxidative stress/lipid peroxidation products in human cultured hepatocytes (HepG2 cells). HepG2 cells were pretreated with niacin (0-0.5 mM) for 24 h. Cells were than stimulated with palmitic acid for 24 h. Reactive oxygen species (ROS, as an index of oxidative stress) production was measured by DCFDA method by measuring the fluorescence.

The in-vitro data on HepG2 cells presented in FIGS. 6 and 7 suggest that niacin targets liver hepatocytes for inhibiting fat accumulation and oxidative products in liver.

Figure 8:
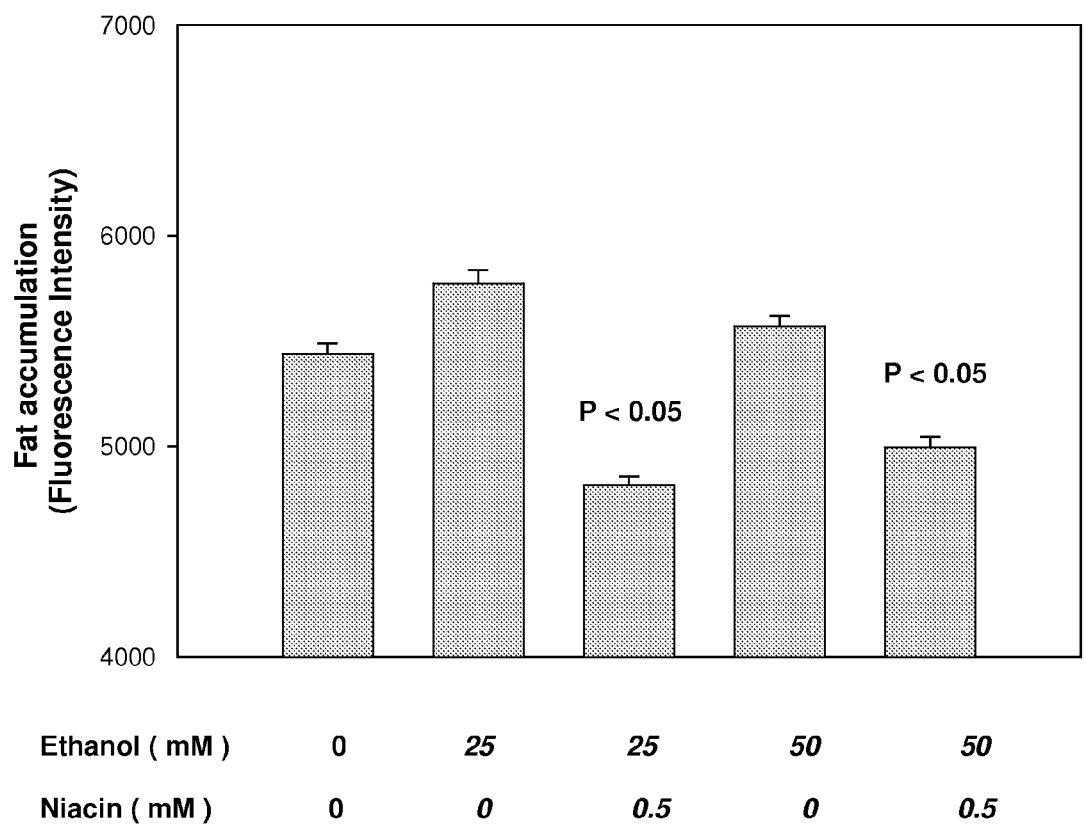

FIG. 8 shows fat accumulation in rats treated with niacin and alcohol. Hep G2 cells were incubated with niacin (0.5 mM) for 24 hours. Cells were then treated with ethanol for 48 hours in the presence or absence of niacin. Cellular fat accumulation was quantitated by nile red O staining and by measuring fluorescence intensity. As shown in FIG. 8, treatment of cultured hepatocytes with niacin significantly inhibited alcohol-induced fat accumulation, P values shown are compared to respective ethanol treated cells.

DETAILED DESCRIPTION OF THE INVENTION

"An effective amount" refers to an amount of niacin, its metabolites or synthetic derivatives, which reduces the severity, occurrence or frequency of the symptoms displayed in those in need of treatment, or prevents the further development of such symptoms. Such an amount can be determined by those of skill in the art based in part on the concentrations known to be effective on rats and also from niacin clinical studies performed on human subjects.

"A reduction" in symptoms in the context of "a reduction in symptoms displayed in those in need of treatment" is defined as a reduction in one or more of the symptoms displayed in those subjects in need of treatment (as noted above), as measured by clinical tests, experimental assays, diagnostic tests or visually by a clinician.

The term "inhibiting and/or reversing" means a lessening of the symptoms mentioned, whether it is determined objectively or subjectively, to a degree that is observed either within "normal" levels (as observed in control subjects) or levels above such normal subjects but lower than that observed without niacin treatment.

The term "convention drugs" refers to drugs that are conventionally used to treat subjects in need of treatment with those symptoms or diseases described. For instance such drugs used to treat type 2 diabetes are well known to those of skill in the art.

Pharmaceutically acceptable or appropriate carriers can be, but not limited to, organic or inorganic, solid or liquid excipient which is suitable for the selected mode of application such as oral application or injection, and administered in the form of a conventional pharmaceutical preparation. Such preparation includes solid such as tablets, granules, powders, capsules, and liquid such as solution, emulsion, suspension and the like. Said carrier includes starch, lactose, glucose, sucrose, dextrine, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

The term "neutraceutical" as used herein means a food stuff (as a fortified food or a dietary supplement) that provides health benefits. Nutraceutical foods are not subject to the same testing and regulations as pharmaceutical drugs.

Disclosed is a new indication that niacin (nicotinic acid), its formulations, metabolites, derivatives or analogs can be used as therapeutic agent(s) in the treatment of fatty liver disease, including non-alcoholic fatty liver disease (NAFLD), alcoholic and other forms of fatty liver disease. As written in this invention form, fatty liver disease is synonymous with steato-hepatitis and NAFLD with non-alcoholic steato-hepatitis (NASH).

Excessive accumulation of triglycerides (fat) in hepatocytes is the hallmark of NAFLD, which is strongly associated with insulin resistance. In addition to excessive fat accumulation in liver, hepatic inflammatory events and oxidative stress have also been thought to contribute to the progression of liver damage associated with NAFLD. Specifically, pro-inflammatory cytokines released by hepatocytes or activated neutrophils further exacerbate hepatic tissue injuries induced by excessive fat accumulation.

If untreated, NAFLD leads to liver failure, cirrhosis and its complications, need for liver transplantation It is often associated with increased risk of developing cardiovascular disease resulting in increased morbidity and mortality. Additionally, hepatic steatosis is also a risk factor for developing hepatocellular carcinoma.

Experimental Procedures

Animals and Diets: Adult male Sprague-Dawley rats (250-300 g) were obtained from Charles River Labs (Wilmington, Mass.). Nicotinic acid (niacin) was obtained from Sigma-Aldrich Corporation (St, Louis, Mo.). Custom-prepared diets including control (Lab Dyets #100000), High-fat (Lab Dyets #101447), and High-fat diet containing 0.5% and 1% niacin were obtained from Dyets Inc (Bethlehem, Pa.). Control diet is a low-fat diet consisting of 12% of total calories from fat as corn oil, and most of the fat is linoleic acid. The High-fat (HF) diet contained 60% of total calories as lard and 2% corn oil and is enriched in oleic acid and the saturated fatty acids palmitic and stearic. This High-fat diet has been previously used to induce NAFLD in rats (22). Seven rats in each of the 4 groups were randomized and fed the following diets for 4 weeks: Group I: control diet; Group II: HF diet, Group III: HF+0.5% niacin diet; Group IV: HF+1% niacin. The rats were placed on a 12-h day/night cycle and provided ad libitum access to food and water. The study was approved by the institutional IACUC and Research and Development committees. After the feeding period, rats were fasted 16-18 h, anesthetized, and blood and liver samples were collected for biochemical and histological analyses.

Serum and liver triglyceride and cholesterol: Serum triglyceride and total cholesterol were measured by commercially available assay kits from Wako Diagnostics (Richmond, Va.). Total lipid was extracted from liver samples (about 0.25 g) with chloroform-methanol mixture (2:1) and washed with 0.73% sodium chloride solution. The organic and aqueous phases were separated by centrifugation at 2000 rpm for 10 min. The organic phase containing total lipid was dried completely under nitrogen and lipid extract reconstituted in isopropanol. An aliquot of lipid extract was used to measure triglycerides and total cholesterol using assay kits from Wako Diagnostics.

Measurement of serum and liver thiobarbituric acid-reactive substances (TBARS): Serum and liver TBARS were measured as an index of lipid peroxidation products.

Liver histology: Liver samples were fixed in 10% formalin and embedded in paraffin. Sections (5 μm) were stained with hematoxylin and eosin and evaluated by a pathologist who was blinded from the experimental groups and conditions. Sections were subjected to semi-quantitation for assessing steatosis.

Statistical analysis: Data presented are mean+S.E. Statistical analyses for the two groups were made using a two-tailed Student's t test, and $p<0.05$ was considered statistically significant.

Results

Food intake, body weight, and liver weight: During the course of the study, rats in each group consumed an average of 20 g diet. There was no difference in diet consumption between the groups. After 4 weeks of the feeding period, rats in high-fat fed group (Group II) exhibited significantly higher body weight than in control diet fed rats (Group I, FIG. 1a). Inclusion of niacin at 0.5% (Group III) or 1% (Group IV) level in the high-fat diet had no effect on body weight of rats as compared to high-fat fed rats (Group II).

Figure 1:
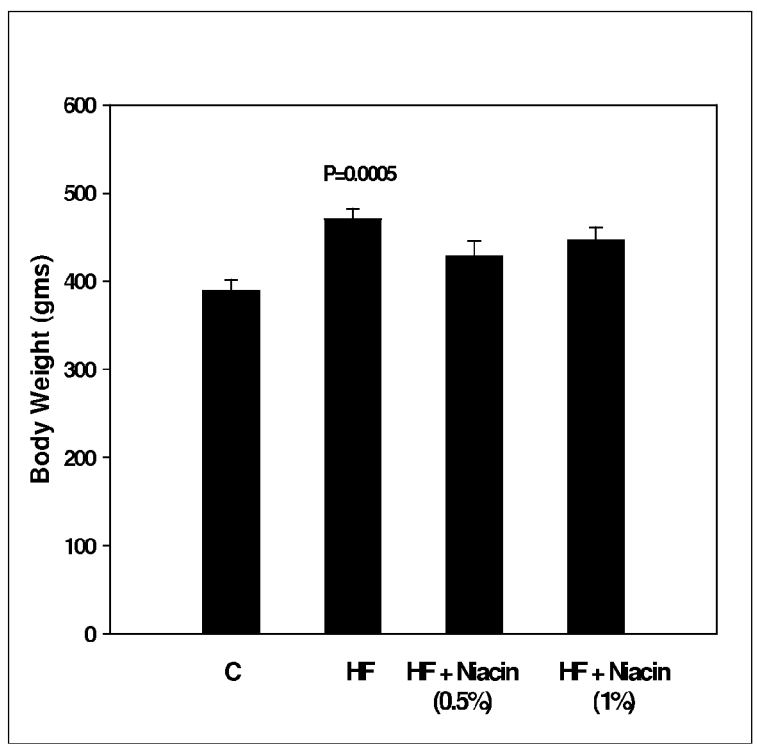
FIG. 1 shows the effect of niacin on body and liver weights. Rats were fed ad libitum quantities of control diet (C), High-fat diet (HF), HF+0.5% niacin, and HF+1% niacin for 4 weeks. 1A: Body weight of rats, 1B: liver weight of rats. P-values shown on HF group represent comparison to control group, and on HF+niacin groups are compared to HF group.
Figure 1:
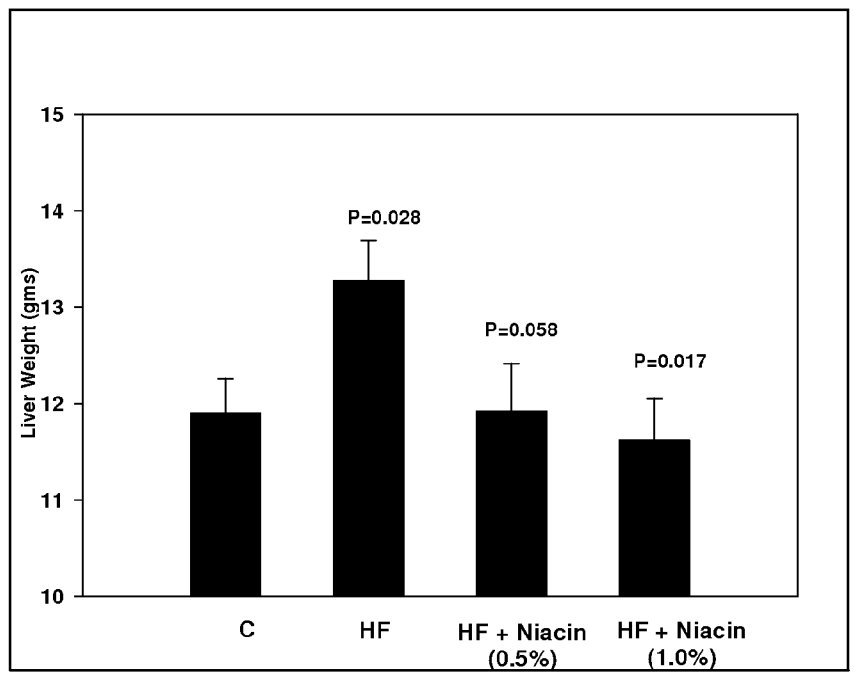

Rats fed high-fat diet had significantly higher liver weight (group II) when compared to rats fed control diet (Group I, FIG. 1b). Addition of niacin at 0.5% or 1% levels completely blocked gain in liver weight induced by high-fat diet (FIG. 1b). Liver weights of rats fed high-fat diet-containing niacin (0.5% or 1%) were similar to those seen in rats fed control diet (FIG. 1b). As far as we know, such findings are novel.

Figure 2:
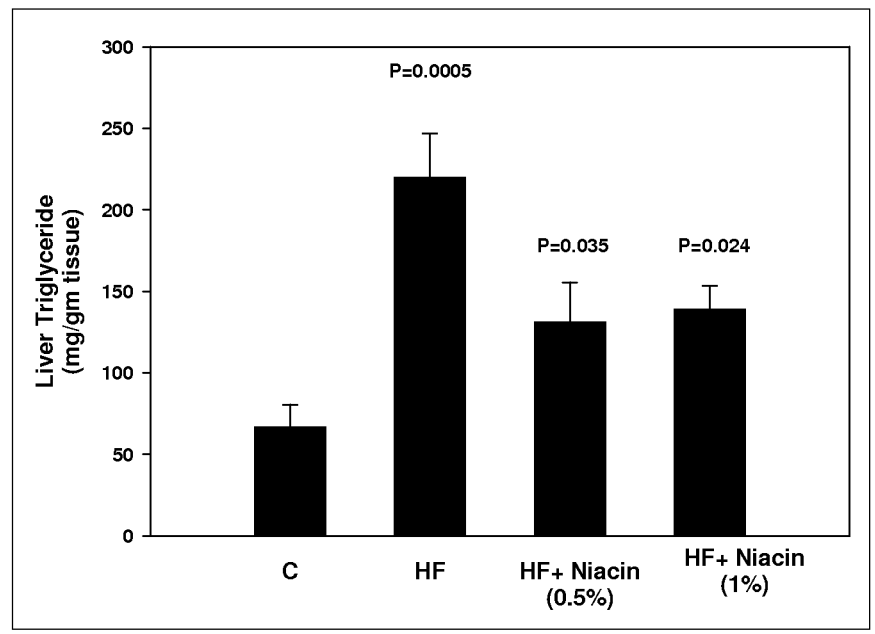
FIG. 2 shows that niacin prevents deposition of triglycerides in liver and serum. Liver and serum triglycerides were measured as noted in Methods. 2A Liver and 2B serum triglycerides are expressed as mg/g of liver and mg/dl of serum respectively. P-values shown on HF group represent comparison to control group, and on HF+niacin groups are compared to HF group.
Figure 2:
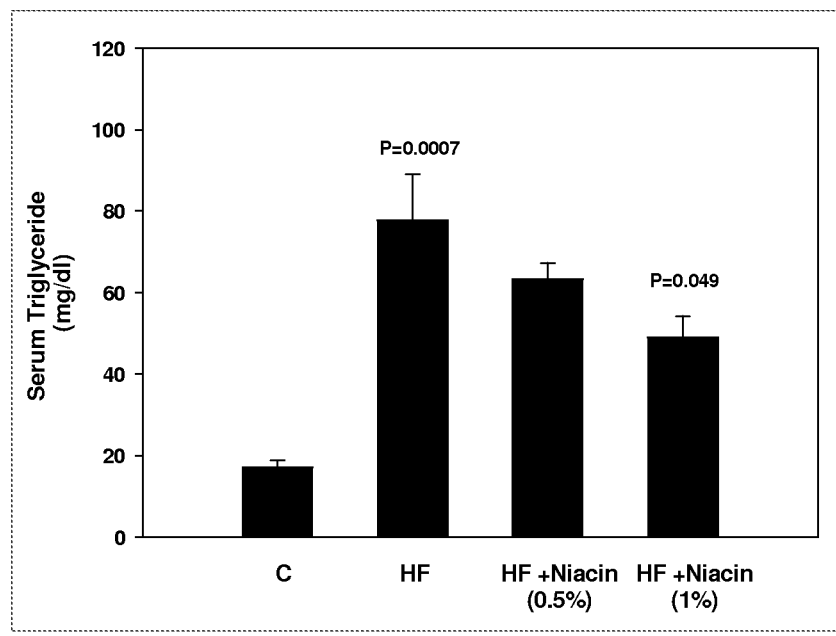

Liver and Serum triglycerides and cholesterol: Feeding of high-fat diet to rats caused a significant and marked deposition of triglycerides in the liver (about 4-fold increase) when compared to rats fed a control diet (FIG. 2a). Niacin addition in the high-fat diet significantly reduced liver triglyceride deposition by about 60% when compared to rats fed high-fat diet (FIG. 2a). Similar to liver, triglyceride levels in serum were also markedly higher (about 5-fold) in rats fed high-fat diet as compared to rats on a control diet (FIG. 2b). Niacin also significantly decreased serum triglyceride levels (FIG. 2b). As far as we know, such findings are novel.

Figure 3:
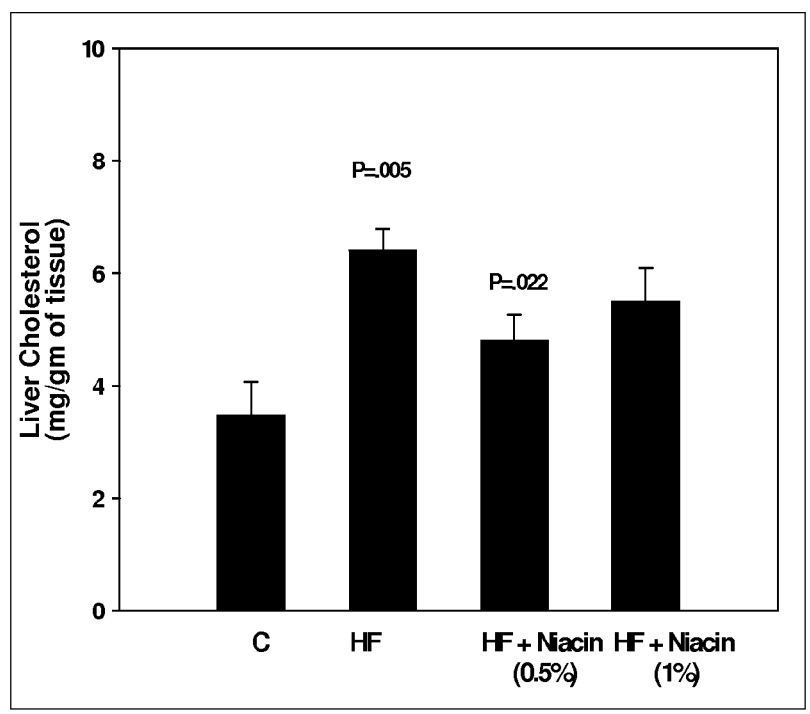
FIG. 3 shows niacin prevents deposition of total cholesterol in 3A liver and 3B serum. Liver and serum total cholesterol levels were measured by an assay kit as noted in Methods. Liver and serum total cholesterol values are expressed as mg/g of liver and mg/dl of serum respectively. P-values shown on HF group represent comparison to control group, and on HF+niacin groups are compared to HF group.
Figure 3:
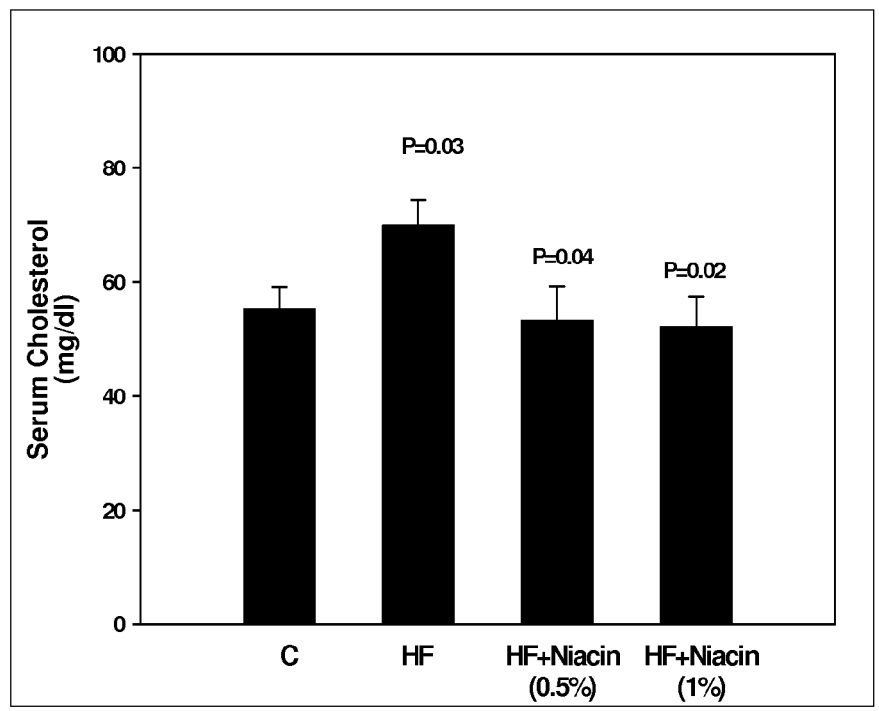

In addition to triglycerides, serum and liver cholesterol levels were also significantly increased in rats fed high-fat diet as compared to rats on a control diet (FIG. 3a, 3b). Inclusion of niacin (0.5% and 1%) in high-fat diet significantly decreased both serum and liver cholesterol levels when compared to rats fed high-fat diet (FIG. 3a, 3b). As far as we know, such findings are novel.

Figure 4A:
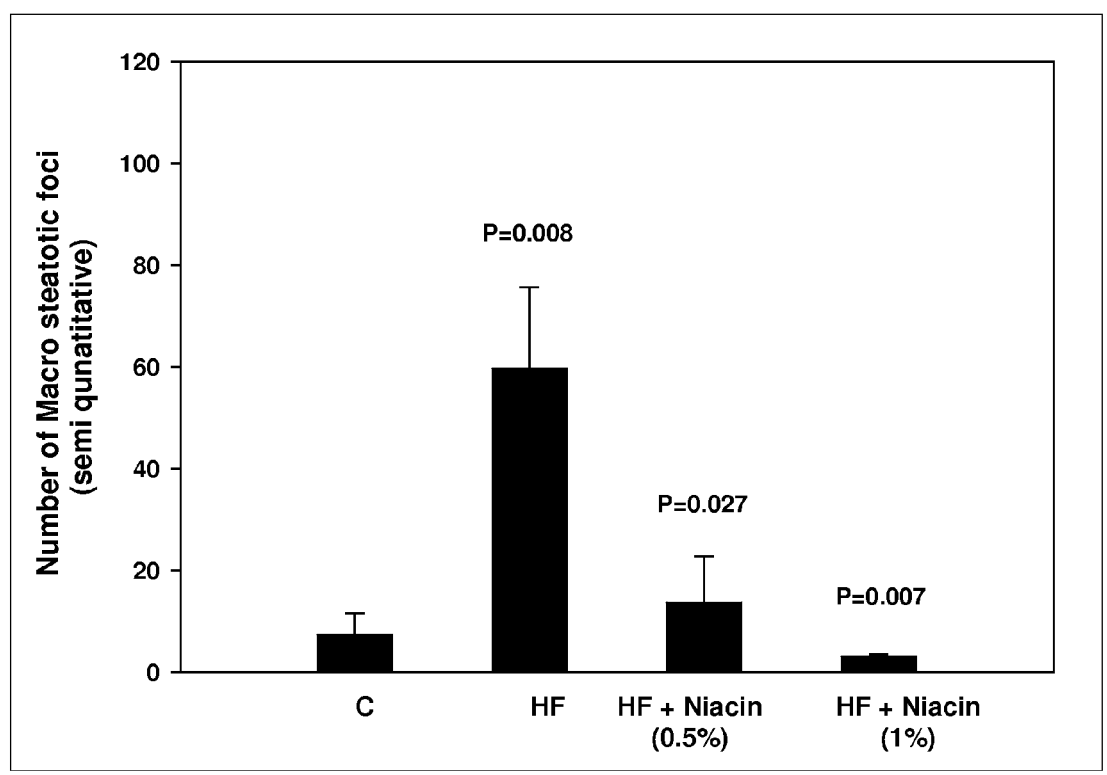
FIG. 4 shows niacin prevents the development of hepatic steatosis. 4A: Sections of the liver stained with haematoxylin and eosin were semi-quantitatively evaluated for hepatic steatosis by measuring the number of macro steatotic bodies. P-value shown on HF group represents comparison to control group, and on HF+niacin groups are compared to HF group. 4B: Representative histological images of liver sections stained with haematoxylin and eosin. Prominent macrosteatosis and microsteatosis were noted in liver sections of rats fed high fat (HF) diet when compared to liver sections of control rats. The degree of lipid present is markedly greater in HF diet fed liver sections than in controls. Both macro- and microsteatosis is significantly decreased in niacin treated rats when compared to liver sections of rats fed HF diet.
Figure 4B:
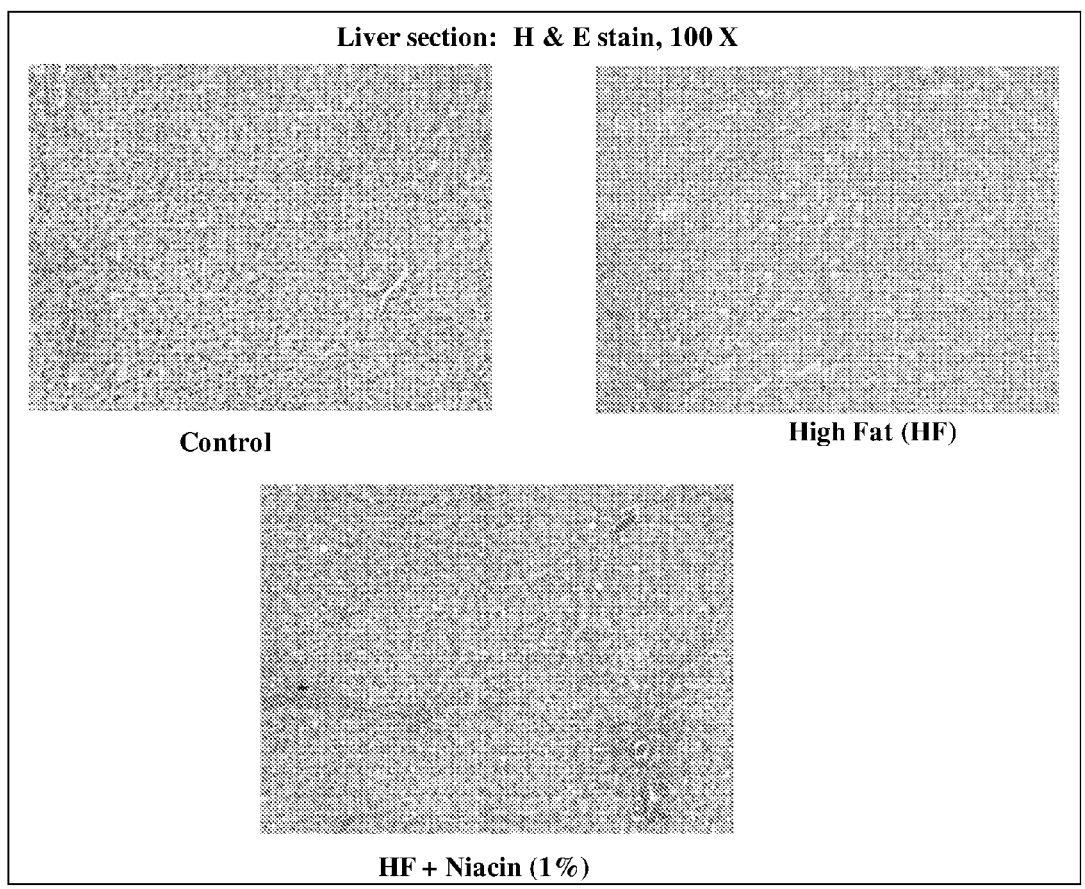

Liver histological evaluation: Histological examination of liver sections stained with haematoxylin and eosin were performed to determine hepatic macrovesicular steatosis, necrosis, and inflammation. For semi-quantitative analysis, numbers of macrosteatotic foci were counted in liver sections. As shown in FIG. 4, a markedly increased number of macrosteatotic foci were observed in liver sections of rats fed high-fat diet as compared to rats fed a control diet. Inclusion of niacin in the high-fat diet (0.5% and 1%) almost completely blocked high-fat induced appearance of macrosteatotic foci, and the number of macrosteatotic foci were similar to those observed in rats fed a control normal diet. As far as we know, such findings are novel.

Figure 5:
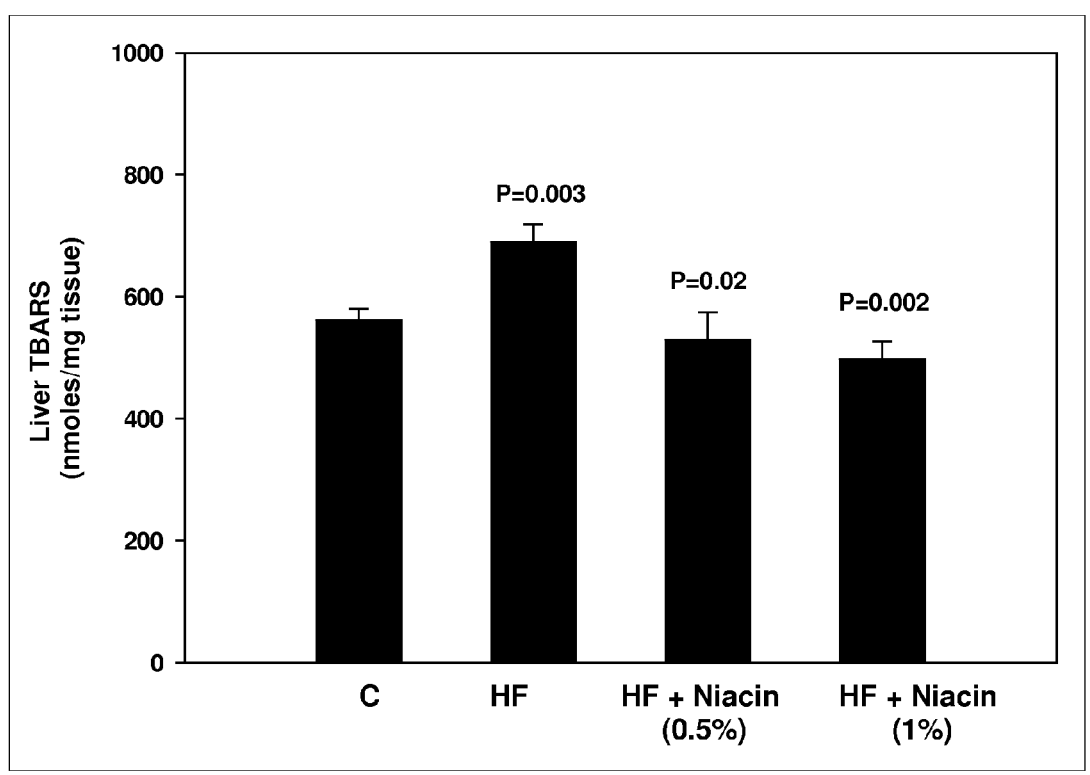
FIG. 5 shows niacin inhibits liver lipid peroxidation products. Thiobarbituric acid reactive substances (TBARS) were measured to assess the levels of lipid peroxidation products in liver extracts. P-value shown on HF group represents comparison to control group, and on HF+niacin groups are compared to HF group.

Liver lipid peroxidation products: TBARS levels in liver extracts were measured to assess the degree of lipid peroxidation products and oxidative stress occurred in liver tissue. Niacin addition to the high-fat diet (at 0.5% and 1% level) significantly inhibited liver TBAR levels as compared to the TBAR levels seen in rats fed high-fat diet (FIG. 5). As far as we know, such findings are novel.

FIG. 8 shows that niacin significantly inhibited ethanol induced fat accumulation in human hepatocytes. This indicates that niacin is effective in preventing, treating or reversing AFLD in subjects in need of treatment.

Discussion

A high-fat diet administered to rats is a well characterized in-vivo model for NAFLD, and has been extensively used for understanding the pathogenesis of NAFLD and for interventional studies (2, 22-26). The key features of high-fat induced NAFLD in rats include micro/macro vesicular steatosis, increased formation of lipid oxidative products, hepatic inflammation, and early fibrosis, which are characteristic pathologic elements seen in the evolution of NAFLD and NASH in humans. Thus, high-fat-induced NAFLD in rats has been viewed as a realistic experimental model for initial testing of pharmacological agents for the prevention and/or regression of NAFLD and NASH.

Accumulation of excess fat in the liver "hepatic steatosis" is the early pathobiological event and subsequently leads to FLD, and advanced NAFLD forms including non-alcoholic steato-hepatitis (NASH) which may lead to liver fibrosis and cirrhosis. Thus, excess fat accumulation is considered as an early index of NAFLD. In our studies, we have shown that niacin prevents the development of hepatic steatosis.

We have not assessed BMI, ultrasound evidence of fat, and features of metabolic syndrome as in humans. Regarding evidence of fat accumulation in livers, our study used more sensitive methods than the ultrasound evidence of fat as performed in human. We utilized histological assessment of fat accumulation in liver using lipid staining of liver sections and biochemical analysis of liver triglycerides and cholesterol. These are accurate assessment of the evidence of fat accumulation in livers.

tablets, capsules, or drops); by gastric feeding tube, duodenal feeding tube, or gastrostomy; and rectally (as suppositories). Parenteral administration includes, but is not limited to, intravenous; and intra-arterial.

Table 1 lists some possible niacin formulations or preparations, Table 2 shows examples of possible niacin metabolites, and Table 3 shows examples of niacin derivatives that could be used in subjects in need of treatment and/or to prevent and/or reversal of fatty liver disease (alcoholic and non-alcoholic).

TABLE 1

| Niacin Formulation/Preparation | Manufacturer |
|---|---|
| Immediate-release niacin (OTC) | Rugby, Westbury, NY |
| | Squibb, Princeton, NJ |
| | Solaray, Park City, UT |
| | Etc |
| | |
| | |
| Sustained-release niacin (also referred as: timed-release, controlled-release, slow-release, prolonged-release, long acting, intermediate-release, etc) | |
| .....Slo-Niacin | Upsher-Smith, Minneapolis, MN, |
| .....Enduracin | Endurance Products Co., Tigard, OR |
| | |
| | Vitamin Shoppe, North Bergen, NJ, |
| No flush niacin (inositol hexanicotinate) | Solaray Park City, UT, Etc. |
| | |
| | |
| Extended-release niacin | Abbott Laboratories* |
| .....Niaspan* | Merck* |
| .....Tredaptive* (Extended-release niacin with laropiprant) | |
| .....* | |

The present in-vivo study in rats is mainly focused on the effect of niacin on the prevention of hepatic steatosis in a well established high-fat-induced NAFLD model in rats. Our data indicate that niacin (at 0.5% and 1% in the diet) markedly and significantly prevented the development of hepatic steatosis as assessed by histological deposition of steatotic foci and fat content in liver. Specifically, it is important to note that niacin almost completely normalized liver pathology with respect to the deposition of steatotic bodies, an initial "first hit" insult involved in the development of NAFLD. These studies, for the first time, suggest that niacin can prevent high-fat-induced NAFLD in rat model. Based on the diet intake and the dosages of niacin used in the diet, we estimate that rats consumed 0.1 g and 0.2 g niacin per day with high-fat diet containing 0.5% and 1% niacin. Niacin doses of 0.5% and 1% in the diet were comparable to those reported previously in animal studies related to the effect of niacin on plasma lipids (27). Although these doses of niacin used (per kg body weight) in our rat studies are much higher (about 4.6-9.3-fold) than the currently recommended niacin doses in humans for treating cardiovascular disease, our data provide proof-of-concept that niacin can be used as a preventive therapy for NAFLD. We estimate that 0.5-3 g/daily in oral tablet form would be the effective dose to give to humans, and 1-2 g/daily dose would be preferred dose range. The dosages of metabolites, analogs or formulations of niacin can be the same or different.

It may be possible to introduce niacin or its metabolites, or their derivatives/analogs or formulations thereof into human subjects using enteral or parenteral administration. Enteral administration includes, but not limited to, by mouth (as

TABLE 2

Examples of Niacin Metabolites

Niacin Metabolites

Nicotinuric acid
Nicotinamide
6-hydroxy nicotinamide
N-methylnicotinamide
Nicotinamide-N-oxide
N-methyl-2-pyridone-5-carboxamide
N-methyl-4-pyridone-5-carboxamide

TABLE 3

Examples of Niacin Derivatives

Niacin Derivatives (commercially available)

Acifran
Acipimox
Niceritrol
Isonicotinic acid
Isonicotinohydrazide
Pyridine carboxylic acid derivatives
3-pyridine acetic acid
5-methylnicotinic acid
Pyridazine-4-carboxylic acid
Pyrazine-2-carboxylic acid,
Etc In our studies, we have shown that niacin significantly inhibited lipid peroxidation products in liver extracts. Since lipid peroxidation and inflammatory events play a critical "second hit" in the progression of NAFLD and NASH, the ability of niacin to inhibit the generation of lipid peroxidation products would be important in preventing the "second hit" insult or injury involved in the progression of NAFLD and NASH.

Findings from this study indicate the usefulness of niacin in the prevention of hepatic steatosis, however our data do not provide experimental evidence whether niacin therapy for short period of time can also be effective in regression of established NAFLD and NASH. Since the progression of hepatic steatosis to advanced NAFLD and NASH takes several years, the beneficial effect of niacin on the regression of NAFLD and NASH would require long-term treatment with niacin for at least 5 years. In a recent small study with 9 patients with NAFLD and obesity, niacin (2000 mg/day) treatment for 16 weeks had no effect on intrahepatic triglyceride content (28). In view of this short treatment regimen (4 months), it is not surprising that niacin had no effect on the regression of NAFLD in this study. Nevertheless, our observation suggests that niacin can effectively prevent the development of hepatic steatosis (that is, an early indicator of NAFLD) and subsequent progression to NASH.

Acknowledgements:

This work was supported by a small grant from the Southern California Institute of Research and Education (SCIRE), a non-profit arm/affiliate of the Long Beach Veterans Affairs Healthcare System which is affiliated to the University of California, Irvine, Calif.

REFERENCES

All References Disclosed Herein are Incorporated by Reference in their Entirety 1. Doege H, et al. Silencing of hepatic fatty acid transporter protein 5 in vivo reverses diet-induced non-alcoholic fatty liver disease and improves hyperglycemia. J. Biol. Chem. 283:22186-22192, 2008
2. Samuel V T, et al. Mechanism of hepatic insulin resistance in non-alcoholic fatty liver disease. J. Biol. Chem. 279: 32345-32353, 2004.
3. Postic C, Girard J. Contribution of de novo fatty acid synthesis to hepatic steatosis and insulin resistance: lessons from genetically engineered mice. J. Clin. Invest. 118:829-838, 2008.
4. Adams L A, Lindor K D. Nonalcoholic fatty liver disease. Ann. Epidemiol. 17:863-869, 2007.
5. Yamaguchi K. et al Inhibiting triglyceride synthesis improves hepatic steatosis but exacerbates liver damage and fibrosis in obese mice with non-alcoholic steatohepatitis. Hepatology 45:1366-1374, 2007.
6. Abdelmalek M F, Diehl A M. Nonalocoholic fatty liver disease as a complication of insulin resistance. Med. Clin. North Am. 91:1125-1149, 2007.
7. Charlton M. Nonalcoholic fatty liver disease: a review of current understanding and future impact. Clin. Gatroenterol. Hepatol. 2:1048-1058, 2004.
8. Pagano G, Pacinim M, Musso G, et al. Nonalcoholic steatohepatitis, insulin resistance, and metabolic syndrome: further evidence for an etiologic association. Hepatology 35:367-372, 2002.
9. Day C P, James O F. Hepatic steatosis: Innocent bystander or guilty party? Hepatology 27:1463-1466, 1998.
10. Day C P. James O F. Steatohepatitis: a tale of two "hit"? Gastroenterology. 114:842-845, 1998.
11. Wanless I R. Lentz J S. Fatty liver hepatitis (steatohepatitis) and obesity: an autopsy study with analysis of risk factors. Hepatology 12:1106-1110, 1990.
12. Ludwig J. Viggiano T R, McGill D B, Ott B J. Nonalcoholic steatohepatitis: Mayo clinic experience with a hitherto unnamed disease. Mayo Clinic Proc. 55:434-438, 1980.
13. Adams L A, Angulo P. Treatment of non-alcoholic fatty liver disease. Postgrad. Med. J., 82:315-322, 2006.
14. Ahmed M H, Byrne C D. Current treatment of non-alcoholic fatty liver disease. Diabetes, Obesity and Metabolism. 11:188-195, 2009.
15. Belfort R, Harrison S A, Brown A K, et al. A placebo-controlled trial of pioglitazone in subjects with non-alcoholic steatohepatitis. N. Eng. J. Med. 355:2297-2307, 2006.
16. Sanyal A, Chalasani N, Kowdley K V, et al. Pioglitazone, vitamin E, or placebo for nonalcoholic steatohepatitis. N. Eng. J. Med. 362:1675-1685, 2010.
17. Caldwell S H, Hespenheide E E, Dedick J A, Iezzoni J C, Battle E H, Shppard B L. A pilot study of thiazolidinedione, troglitazone, in nonalcoholic steatoheatatitis. Am. J. Gastroenerol. 96:519-525, 2001.
18. Neuschwander-Tetri B A, Brunt E M, Wehmeier K R, Oliver D, Bacon B R. Improved nonalcoholic steatohepatitis after 48 weeks of treatment with the PPAr-gamma ligand rosiglitazone. Hepatology 38:1008-1017, 2003.
19. Sanyal A J. Mofrad P S, Contos M J, et al. A pilot study of vitamin E versus vitamin E and pioglitazone for the treatment of nonalcoholic steatohepatitis. Clin. Gastroenerol. Hepatol. 2:1107-1115, 2004.
20. Lavine J E. Vitamin E treatment of nonalcoholic steatohepatitis in children: a pilot study. J. Pediatr. 136:734-738, 2000.
21. Harrison S A, Torgerson S, Hayashi P, Ward J, Schenker S. Vitamin E and vitamin C treatment improves fibrosis in patients with nonalcoholic steatohepatitis. Am. J. Gastroenterol. 98:2485-2490, 2003.
22. Carmiel-Haggai M, Cederbaum A I, Nieto N. A high-fat diet leads to the progression of non-alcoholic fatty liver disease in obese rats. FASEB J. 19:136-138, 2005.
23. Lieber C S, Leo M A, Mak K M, Xu Y, Cao Q, Ren C, Ponomarenko A, DeCarli L M. Model of nonalcoholic steatohepatitis. Am. J. Clin. Nutr. 79:502-509, 2004.
24. Charbonneau A, Unson C G, Lavoie J-M. High-fat diet-induced hepatic steatosis reduces glucagon receptor content in rat hepatocytes: potential interaction with acute exercise. J. Physiol. 579:255-267, 2007.
25. Choi C S, Savage D B, Kulkarni A, et al. Suppression of diacylglycerol acyltransferase-2 (DGAT2), but not DGAT1, with antisense oligonucleotides reverse diet-induced hepatic steatosis and insulin resistance. J. Biol. Chem. 282:22678-22688, 2007.
26. Hong X Z, Li L D, Wu L M. Effects of fenofibrate and xuezhikang on high-fat diet-induced non-alcoholic fatty liver disease. Clin. Expt. Pharmacol. Physiol. 34:27-35, 2007.
27. Hernandez M, Wright S D, Cai T Q. Critical role of cholesterol ester transfer protein in nicotinic acid-mediated HDL elevation in mice. Biochem. Biophys. Res. Commun. 355:1075-1080, 2007.
28. Fabbrini E, Mohammed B S, Korenblat K M, Magkos F, Magkos F, McCrea J, Patterson B W, Klein S. Effect of fenofibrate and niacin on intrhepatic triglyceride content, very-low density lipoprotein kinetics, and insulin action in obese subjects with nonalcoholic fatty liver disease. J. Clin. Endocrinol. Metab. 95:2727-2735, 2010.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims.

The invention claimed is:

1. A method for treating the development of fatty liver disease in a subject in need thereof, comprising administering a composition comprising an effective amount of niacin, or a metabolite or derivative thereof, to the subject for a period of more than sixteen weeks.

2. The method of claim 1, wherein fatty liver disease is non-alcoholic fatty liver disease.

3. The method of claim 1, wherein the subject shows signs of obesity, type 2 diabetes, clinical hepatomegaly, high transaminase levels, abnormal liver function tests, elevated body mass index, insulin resistance, high-fat diet consumption, elevated fat accumulation in the liver, hepatomegaly, metabolic syndrome, fat and liver inflammation, liver fibrosis, or any combination thereof.

4. The method of claim 1, wherein the effective amount of niacin is 0.5-3 g/daily in oral tablet form.

5. The method of claim 1, wherein the niacin is in the form of an immediate-release niacin, a timed release niacin, a sustained release-niacin, a no-flush niacin, or an extended-release niacin.

6. The method of claim 1, wherein the niacin metabolite is selected from the group consisting of nicotinuric acid, nicotinamide, 6-hydroxy nicotinamide, N-methylnicotinamide, nicotinamide-N-oxide, N-methyl-2-pyridone-5-carboxamide, and N-methyl-4-pyridone-5-carboxamide.

7. The method of claim 1, wherein the niacin derivative is selected from the group consisting of acifran, acipimox, niceritrol, isonicotinic acid, isonicotinohydrazide, pyridine carboxylic acid derivatives, 3-pyridine acetic acid, 5-methylnicotinic acid, pyridazine-4-carboxylic acid, and pyrazine-2-carboxylic acid.

8. The method of claim 1, wherein the effective amount is administered via enteral or parenteral routes of administration.

9. A method for treating hepatic steatosis in a subject in need thereof, comprising administering an effective amount of niacin, or a metabolite or derivative thereof, to the subject for a period of more than sixteen weeks.

10. The method of claim 1, wherein fatty liver disease is alcoholic fatty liver disease.

11. The method of claim 1, wherein the period is at least five years.

12. The method of claim 9, wherein the period is at least five years.

* * * * *